(12) United States Patent
Miyata et al.

(10) Patent No.: US 9,507,083 B2
(45) Date of Patent: Nov. 29, 2016

(54) OPTICAL TRANSMISSION ELEMENT

(71) Applicant: OLYMPUS CORPORATION, Tokyo (JP)

(72) Inventors: Akihito Miyata, Akiruno (JP); Yuki Ishikawa, Koganei (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/130,068

(22) Filed: Apr. 15, 2016

(65) Prior Publication Data

US 2016/0231505 A1 Aug. 11, 2016

Related U.S. Application Data

(63) Continuation of application No. PCT/JP2014/075911, filed on Sep. 29, 2014.

(30) Foreign Application Priority Data

Dec. 13, 2013 (JP) .................................. 2013-258620

(51) Int. Cl.
| | |
|---|---|
| *G02B 6/44* | (2006.01) |
| *C08F 24/00* | (2006.01) |
| *G02B 6/02* | (2006.01) |
| *G02B 6/08* | (2006.01) |
| *G02B 23/26* | (2006.01) |
| *C03C 25/10* | (2006.01) |
| *C03C 25/40* | (2006.01) |
| *C03C 25/30* | (2006.01) |

(52) U.S. Cl.
CPC ......... *G02B 6/02395* (2013.01); *C03C 25/106* (2013.01); *C03C 25/30* (2013.01); *C03C 25/40* (2013.01); *G02B 6/08* (2013.01); *G02B 23/26* (2013.01)

(58) Field of Classification Search
USPC ................................................. 385/117, 145
See application file for complete search history.

(56) References Cited

U.S. PATENT DOCUMENTS 6,242,058 B1  6/2001  Bahadur et al.

FOREIGN PATENT DOCUMENTS

| JP | 2003-533428 A | 11/2003 |
| JP | 4229890 B2 | 2/2009 |
| JP | 2010-224174 A | 10/2010 |

OTHER PUBLICATIONS

International Search Report dated Dec. 16, 2014 issued in PCT/JP2014/075911.
Japanese Office Action dated Aug. 25, 2015 issued in JP 2015-527611.
English translation of International Preliminary Report on Patentability dated Jun. 23, 2016 together with the Written Opinion received in related International Application No. PCT/JP2014/075911.

*Primary Examiner* — Eric Wong
(74) *Attorney, Agent, or Firm* — Scully, Scott, Murphy & Presser, P.C.

(57) ABSTRACT

An optical transmission element according to an embodiment comprises a fiber and a covering layer. The fiber includes a core made of glass and a cladding made of glass covering an outer periphery of the core. The covering layer covers an outer periphery of the cladding and includes a plurality of alkyl groups which are not fluorine-substituted wherein each of the alkyl groups is bonded to the cladding via a siloxane bond and wherein the alkyl groups are represented by $CH_3(CH_2)_n$— wherein m is an integer of 7 or more.

8 Claims, 3 Drawing Sheets

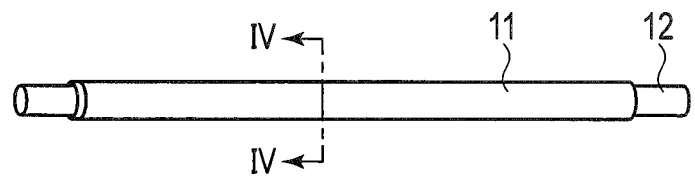
F I G. 3
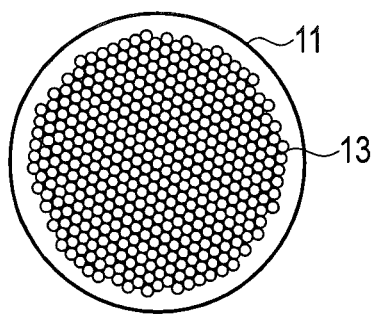
F I G. 4
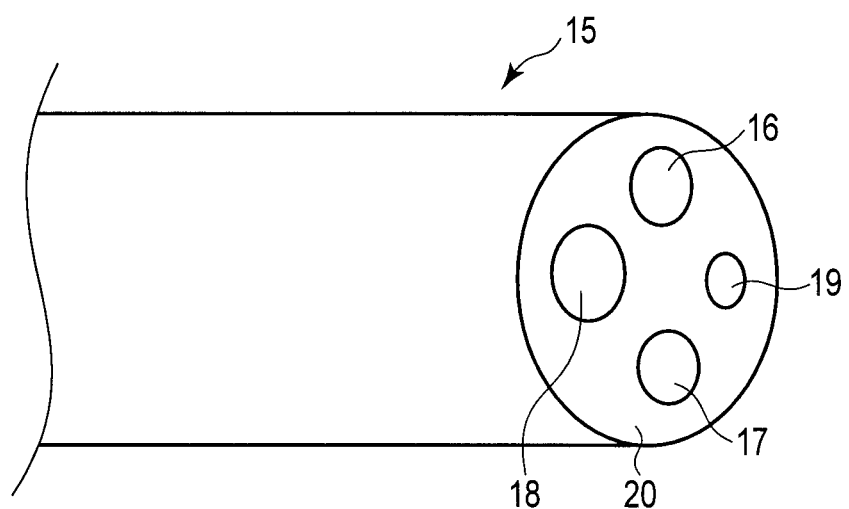
F I G. 5

OPTICAL TRANSMISSION ELEMENT

CROSS-REFERENCE TO RELATED APPLICATIONS

This application is a Continuation Application of PCT Application No. PCT/JP2014/075911, filed Sep. 29, 2014 and based upon and claiming the benefit of priority from Japanese Patent Application No. 2013-258620, filed Dec. 13, 2013, the entire contents of all of which are incorporated herein by reference.

BACKGROUND OF THE INVENTION

1. Field of the Invention

Embodiments of the present invention relate to an optical transmission element, an image guide or a light guide which includes a plurality of the optical transmission elements, and an endoscope including at least one of the image guide and the light guide.

2. Description of the Related Art

In a conventional endoscope, a glass optical fiber containing lead is passed through an insertion portion of the endoscope in order to secure brightness during observation. Such a lead-containing optical fiber is used to transmit illumination light toward a tip part from a light source.

The lead-containing optical fiber has excellent transmissivity and light distribution properties. However, since detrimental substances such as lead are strictly regulated, the development of a lead-free optical fiber has been advanced. However, the lead-free optical fiber has higher hardness in physical properties and lower flexibility than those of the lead-containing optical fiber. For this reason, when the lead-free optical fiber is repeatedly severely bent in the tip part of the endoscope, the lead-free optical fiber is disadvantageously apt to be broken. When the optical fiber is broken, the observation performance of the endoscope is deteriorated.

An optical transmission element is disclosed as an optical fiber for solving such a problem in Japanese Patent No. 4229890. In the optical transmission element, a covering layer including a fluorine-substituted alkyl group-containing organic silicon compound (hereinafter, a fluorinated alkylsilane layer) is formed on the outer periphery of a fiber.

BRIEF SUMMARY OF THE INVENTION

An optical transmission element according to an embodiment comprises a fiber and a covering layer. The fiber includes a glass core and a glass cladding covering an outer periphery of the core. The covering layer covers an outer periphery of the cladding and includes a plurality of alkyl groups which are not fluorine-substituted wherein each of the alkyl groups is bonded to the cladding via a siloxane bond and wherein the alkyl groups are represented by $CH_3(CH_2)_n$— wherein m is an integer of 7 or more.

BRIEF DESCRIPTION OF THE SEVERAL VIEWS OF THE DRAWING

FIG. 3 shows an image guide or a light guide according to an embodiment.

FIG. 4 is a cross-sectional view of the image guide or light guide taken along line IV-IV in FIG. 3.

FIG. 5 shows a tip part of an endoscope according to an embodiment.

DETAILED DESCRIPTION OF THE INVENTION

Figure 1:
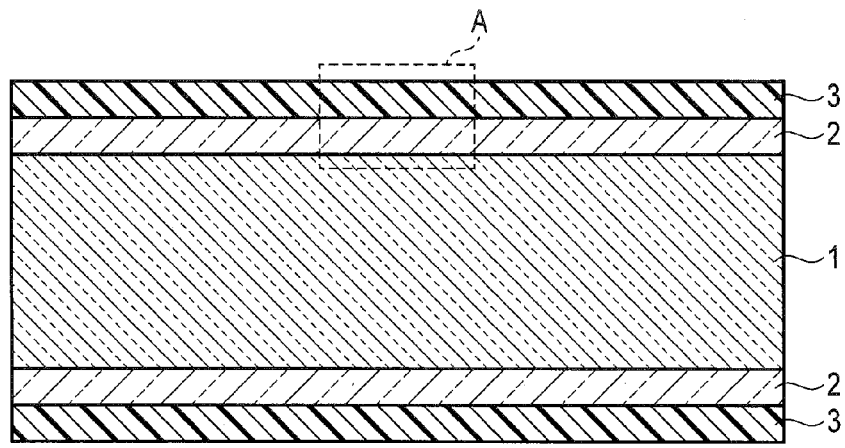
FIG. 1 is an axial cross-sectional view of an optical transmission element according to an embodiment.

A first embodiment of the present invention relates to an optical transmission element. FIG. 1 shows an axial cross-sectional view of an optical transmission element.

The optical transmission element means one used as a light waveguide for propagating a light wave, a signal, an image or the like. The optical transmission element includes, for example, an optical fiber, a light guide, an optical fiber sensor or the like. The optical transmission element may have a circular or rectangular cross-section without particular limitation.

The optical transmission element according to the embodiment includes a fiber and a covering layer 3.

The fiber mainly transmits light in the optical transmission element. The fiber includes a core 1 formed in a cylindrical shape and a cladding 2 covering the outer periphery of the core 1. Both the core 1 and the cladding 2 are made of glass. Preferably, these glasses have high optical transparency, and first glass constituting the core 1 has a higher refractive index than that of second glass constituting the cladding 2. As the first glass and the second glass, silica glass can be used, for example.

The covering layer 3 mainly protects the fiber and adjusts the adhesiveness between a plurality of optical transmission elements when the optical transmission elements are bundled. The covering layer 3 covers the outer periphery of the cladding 2. The thickness of the covering layer 3 is not particularly limited. The thickness may be 1 nm to 100 nm, and is, for example, about 10 nm. When the covering layer 3 is too thin, the fiber cannot sufficiently be protected. On the other hand, when the covering layer 3 is too thick, the ratio of the cross-sectional area of the fiber to the cross-sectional area of the optical transmission element is decreased, which may cause a decrease in the transmitting efficiency of light.

Figure 2:
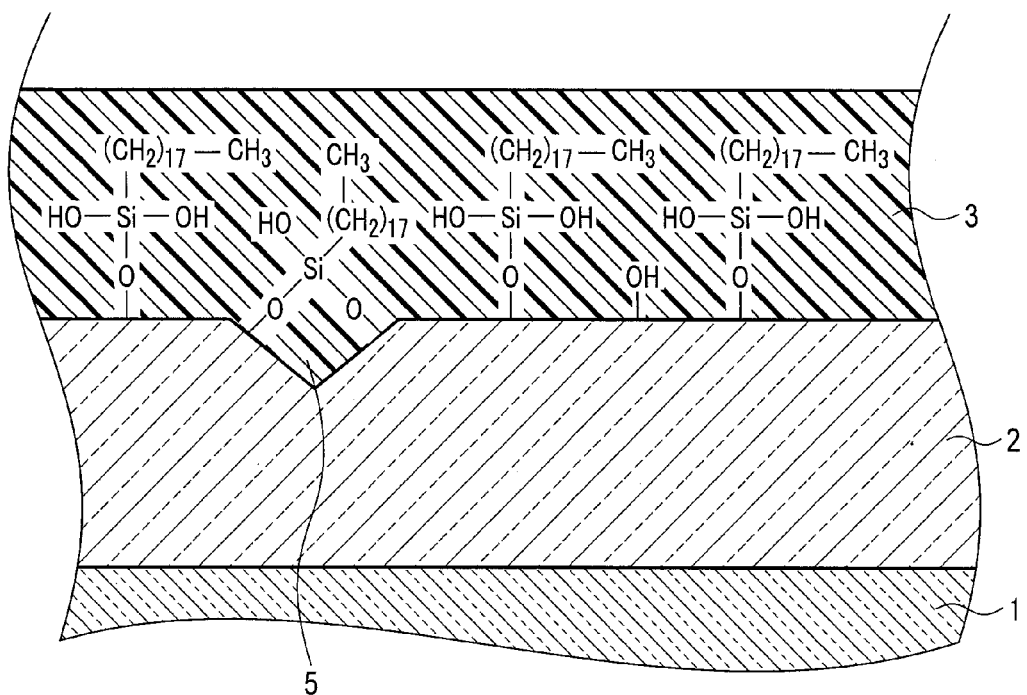
FIG. 2 is an axial cross-sectional view of an optical transmission element according to an embodiment, which represents a magnified view of region A surrounded with a dashed line in FIG. 1.

The covering layer 3 includes a plurality of alkyl groups. Each of the alkyl groups is bonded to the cladding via a siloxane bond. FIG. 2 shows an axial cross-sectional view of an optical transmission element according to an embodiment, which represents a magnified view of region A surrounded with a dashed line in FIG. 1. In FIG. 2, $CH_3$—$(CH_2)_{17}$— is described as an example of the alkyl group. This alkyl group is bonded to the cladding 2 via a —Si—O— bond. In FIG. 2, an alkyl group bonded to a crack 5 occurring on the outer peripheral surface of the cladding exists. As in the alkyl group, an alkyl group may be bonded to the cladding 2 via two or more —Si—O— bonds sharing a Si atom. Alternatively, a Si atom may have a hydroxyl group which is not bonded to the cladding 2. The hydroxyl group which is not bonded to the cladding 2 may be condensed by dehydration with a hydroxyl group of an adjacent Si atom or a hydroxyl group existing on the surface of the cladding 2 to produce a further —Si—O-bond. The alkyl group is not fluorine-substituted.

The alkyl group is represented by the chemical formula $CH_3(CH_2)_m$—. In the chemical formula, m may be any integer of 0 or more, but it is preferably an integer of 7 or more. m is more preferably an integer of 7 or more and 17 or less, and most preferably 9.

The covering layer may be formed by applying a treatment liquid including alkylsilane which is not fluorine-substituted, to the outer periphery of the cladding 2. The method for applying the treatment liquid is not particularly limited. For example, the treatment liquid can be applied by a die coat method, a spray method, a dipping method, or a shower method. The die coat method refers to a method of passing a fiber through a die while supplying a coating liquid to the die to form a covering layer on the surface of the fiber. The spray method refers to a method of spraying a coating liquid on the surface of a fiber. The dipping method refers to a method of immersing a fiber into a coating liquid. The shower method refers to a method of passing a fiber through a shower of a coating liquid.

An example of alkylsilane included in the treatment liquid is represented by the chemical formula $CH_3(CH_2)_m$—$Si(OR)_n$ $(R')_{3-n}$. In the chemical formula, m may be any integer of 0 or more. m is preferably an integer of 7 or more, more preferably an integer of 7 or more and 17 or less, and most preferably 9. n may be an integer of 0 to 3. R each respectively may be —$CH_3$ or —$CH_2CH_3$. R' each respectively may be —H, —$CH_3$ or —$CH_2CH_3$. An —OR group and an —R' group in the formula change to a hydroxyl group in the treatment liquid, which allows dehydration condensation between the hydroxyl group and a hydroxyl group existing on the surface of the cladding 2.

The treatment liquid may include a surfactant and water in addition to alkylsilane. As the surfactant, a nonionic surfactant can be used, for example. As the nonionic surfactant, sorbitan fatty acid ester can be preferably used; polyoxyethylene sorbitan fatty acid ester can be more preferably used; and polyoxyethylene sorbitan monooleate (20E.O.) can be most preferably used. The nonionic surfactant is suitable in light of low stimulativeness and corrosiveness.

The optical transmission element according to the embodiment is preferably free of lead. That is, the fiber and covering layer constituting the optical transmission element are preferably free of lead.

A solid lubricant may be applied to the outer periphery of the covering layer. Examples of the solid lubricant include talc, boron nitride, molybdenum disulfide, a fluoride resin such as ethylene fluoride, polyacetal, and carbon graphite.

A second embodiment of the present invention relates to an image guide. A third embodiment of the present invention relates to a light guide. In the image guide and the light guide, a plurality of optical transmission elements according to the first embodiment are bundled.

An example of an image guide or light guide according to an embodiment is shown in FIG. 3 and FIG. 4. FIG. 4 shows a cross-sectional view of the image guide or light guide taken along line IV-IV in FIG. 3. In this example, bundled plural optical transmission elements 13 are stored in a jacket tube 11. A ferrule 12 is attached to each of both the ends of the jacket tube.

A fourth embodiment of the present invention relates to an endoscope. The endoscope includes at least one of the image guide according to the second embodiment and the light guide according to the third embodiment.

An example of a tip part of an endoscope according to an embodiment is shown in FIG. 5. In an endoscope 15 in this example, an image guide 16 and a light guide 17 are inserted into a tip element 20. A forceps port 18 used for inserting and removing a treatment tool for collecting a tissue or excising a lesion, and a nozzle 19 for sending out water for cleaning lens or air for swelling a body cavity also are provided in the tip element 20.

The optical transmission element according to the embodiment can achieve an excellent effect which cannot be achieved by a conventional optical transmission element.

Figure 6:
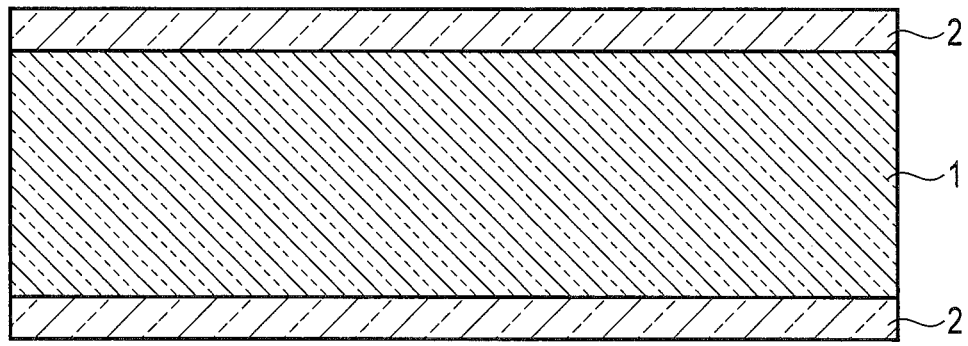
FIG. 6 is an axial cross-sectional view of a conventional optical transmission element which is not covered.
Figure 7:
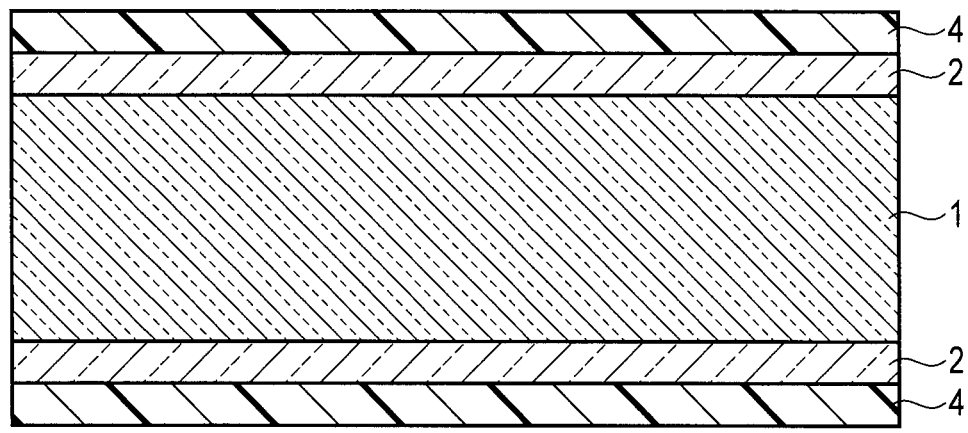
FIG. 7 is an axial cross-sectional view of a conventional optical transmission element which is covered with a fluorinated alkylsilane layer.

An example of a conventional optical transmission element is shown in FIG. 6 and FIG. 7. FIG. 6 shows an axial cross-sectional view of a conventional optical transmission element which is not covered. FIG. 7 shows an axial cross-sectional view of a conventional optical transmission element which is covered with a fluorinated alkylsilane layer 4.

An optical transmission element having no covering layer as shown in FIG. 6 has poorer durability, abrasion resistance, and lubricity than those of an optical transmission element having a covering layer. Particularly, a fiber made of lead-free glass has higher hardness in physical properties and lower flexibility than those of a lead-containing fiber. Therefore, when the image guide or light guide including bundled optical transmission elements which are made of lead-free glass and have no covering layer is repeatedly severely bent in the tip part of the endoscope, it causes the breaking of the fiber in many cases, which leads to a lowering in the observation performance of the endoscope.

An optical transmission element having a fluorinated alkylsilane layer 4 as shown in FIG. 7 has excellent durability, abrasion resistance, and lubricity due to the existence of the fluorinated alkylsilane layer, which can reduce the breaking and deterioration to such an extent that sufficient observation performance is obtained. However, a fluorinated alkyl group in the fluorinated alkylsilane layer is exposed from the surface of the optical transmission element, which deteriorates the adhesiveness between the plurality of optical transmission elements when the optical transmission elements are bundled.

When the image guide or light guide used for the endoscope is manufactured, the plurality of optical transmission elements are bundled and stored in the jacket tube, and then end parts of the bundle are polished. When the end parts of the bundle are polished, the end faces of each of the optical transmission elements are polished to improve optical transparency and align the positions of the end faces of the plurality of optical transmission elements. However, when the adhesiveness between the optical transmission elements is low as in the optical transmission element having the fluorinated alkylsilane layer 4, the fixation of each of the optical transmission elements is insufficient, which makes the polishing difficult. In this case, the edge of the end faces of each optical transmission element is scraped, or some of the end faces of the optical transmission elements are buried. As a result, there is a problem that the observation performance of the endoscope is deteriorated.

On the other hand, the optical transmission element according to the embodiment has excellent durability, abrasion resistance, and lubricity due to the existence of the covering layer, which can reduce the breaking and deterioration. Furthermore, since a fluorine component does not exist on the surface of the optical transmission element, the adhesiveness between the optical transmission elements is improved, which enables suitable polishing. By using such optical transmission elements, the image guide and light guide having excellent durability and optical transparency can be provided. Furthermore, by using such image guide and light guide, an endoscope having excellent observation performance can be provided.

The optical transmission element according to the embodiment may further include a solid lubricant applied to the outer periphery of the covering layer. When the solid lubricant exists on the outer periphery of the covering layer, bundled plural optical transmission elements can be less likely to closely contact with each other, and thus can be prevented from adhesion to each other even if they are subjected to washing, disinfection, and sterilization operations by high temperature and pressure water vapor (autoclave) or a medicinal solution. By the existence of the solid lubricant, breaking resistance can be imparted to the image guide and the light guide.

EXAMPLES

An optical transmission element according to an embodiment was manufactured, and the durability and polishing state of the optical transmission element were evaluated.

<Preparation of Treatment Liquid Including Alkylsilane>

0.01% to 20% of alkylsilane (the general formula $CH_3(CH_2)_m Si(OR)_n(R')_{3-n}$) and 0 to 20% of a dispersing agent were dissolved in water to prepare a treatment liquid. The total amount of alkylsilane and dispersing agent was set to 30% or less. Specific compound names of alkylsilane and dispersing agent were as described in Table 1 below. As the dispersing agent, an organic solvent or a surfactant was used. In this way, 14 treatment liquids were obtained (Examples 1 to 14).

As a comparative example, 0.01% to 10% of a fluorine-substituted alkyl group-containing organic silicon compound was used in place of alkylsilane to prepare a treatment liquid (Comparative Example 1).

<Application of Treatment Liquid to Fiber>

A fiber was immersed into each of the 15 treatment liquids prepared as described above for 10 seconds. Thereby, an optical transmission element including a fiber and a covering layer was obtained.

<Production of Bundle>

The plurality of optical transmission elements produced above was collectively stored in a silicone tube. Subsequently, each end of the silicone tube was inserted into a ferrule, and then sealed with an adhesive, followed by cutting and polishing. In this way, 15 types of bundles were obtained.

In addition, an optical transmission element including only a fiber without having no covering layer was used to produce a bundle (Comparative Example 2).

As a result, 16 types of bundles were produced.

<Evaluation of Durability>

Durability was evaluated for each of the 16 types of bundles produced above.

For the evaluation, a test was carried out by simulating a load applied when a tip part of an endoscope was repeatedly bent to manipulate the endoscope. Specifically, after a higher load than that in the case of manipulating the endoscope was repeatedly applied at given number of times, the number of the broken optical transmission elements was counted. From the result, a breaking rate (%) was calculated according to the following formula:

breaking rate (%)=(number of optical transmission elements broken after test)/(total number of optical transmission elements)×100

The results were summarized in Table 1 below. In Table 1, a bundle having the breaking rate of less than 10% was evaluated as "⊚ (very good)". A bundle having the breaking rate of 10% or more and less than 60% was evaluated as "○ (good)". A bundle having the breaking rate of 60% or more was evaluated as "X (poor)".

<Evaluation of Polishing State>

Furthermore, a polishing state was evaluated for each of the 16 types of bundles produced above.

The state of the end faces of the polished bundle was observed. The results were described in Table 1. In Table 1, a bundle having a usable level for the observation performance of the endoscope was evaluated as "○", and a bundle having an unusable level for the observation performance of the endoscope was evaluated as "X".

TABLE 1

|  | Component name | Substance name | Durability | Polishing state |
|---|---|---|---|---|
| Example 1 | Active ingredient | Methyltrimethoxysilane (m = 0, n = 3, R = CH3) | X | ○ |
|  | Dispersing agent | — |  |  |
|  | Solvent | Water |  |  |
| Example 2 | Active ingredient | Methyltriethoxysilane (m = 0, n = 3, R = CH2CH3) | X | ○ |
|  | Dispersing agent | — |  |  |
|  | Solvent | Water |  |  |
| Example 3 | Active ingredient | Hexyltrimethoxysilane (m = 5, n = 3, R = CH3) | X | ○ |
|  | Dispersing agent | Ethyl alcohol |  |  |
|  | Solvent | Water |  |  |
| Example 4 | Active ingredient | Hexyltriethoxysilane (m = 5, n = 3, R = CH2CH3) | X | ○ |
|  | Dispersing agent | Ethyl alcohol |  |  |
|  | Solvent | Water |  |  |
| Example 5 | Active ingredient | n-octyltriethoxysilane (m = 7, n = 3, R = CH2CH3) | ○ | ○ |
|  | Dispersing agent | Ethyl alcohol |  |  |
|  | Solvent | Water |  |  |
| Example 6 | Active ingredient | Decyltrimethoxysilane (m = 9, n = 3, R = CH3) | ○ | ○ |
|  | Dispersing agent | Ethyl alcohol |  |  |
|  | Solvent | Water |  |  |
| Example 7 | Active ingredient | n-octyltriethoxysilane (m = 7, n = 3, R = CH2CH3) | ○ | ○ |
|  | Dispersing agent | Hexadecyltrimethylammonium chloride |  |  |
|  | Solvent | Water |  |  |
| Example 8 | Active ingredient | Decyltrimethoxysilane (m = 9, n = 3, R = CH3) | ⊚ | ○ |
|  | Dispersing agent | Hexadecyltrimethylammonium chloride |  |  |
|  | Solvent | Water |  |  |

TABLE 1-continued

| | Component name | Substance name | Durability | Polishing state |
|---|---|---|---|---|
| Example 9 | Active ingredient | Octadecyltrimethoxysilane (m = 17, n = 3, R = CH3) | ◎ | ○ |
| | Dispersing agent | Hexadecyltrimethylammonium chloride | | |
| | Solvent | Water | | |
| Example 10 | Active ingredient | Octadecyltriethoxysilane (m = 17, n = 3, R = CH2CH3) | ◎ | ○ |
| | Dispersing agent | Hexadecyltrimethylammonium chloride | | |
| | Solvent | Water | | |
| Example 11 | Active ingredient | Decyltrimethoxysilane (m = 9, n = 3, R = CH3) | ○ | ○ |
| | Dispersing agent | Tetradecyltrimethylammonium chloride | | |
| | Solvent | Water | | |
| Example 12 | Active ingredient | Octadecyltrimethoxysilane (m = 17, n = 3, R = CH3) | ○ | ○ |
| | Dispersing agent | Tetradecyltrimethylammonium chloride | | |
| | Solvent | Water | | |
| Example 13 | Active ingredient | Decyltrimethoxysilane (m = 9, n = 3, R = CH3) | ○ | ○ |
| | Dispersing agent | Polyoxyethylene sorbitan monooleate | | |
| | Solvent | Water | | |
| Example 14 | Active ingredient | Octadecyltriethoxysilane (m = 17, n = 3, R = CH2CH3) | ○ | ○ |
| | Dispersing agent | Polyoxyethylene sorbitan monooleate | | |
| | Solvent | Water | | |
| Comparative Example 1 | Active ingredient | Fluorine-substituted alkyl group-containing organic silicon compound | ◎ | X |
| | Dispersing agent | — | | |
| | Solvent | Fluorine-based solvent | | |
| Comparative Example 2 | Active ingredient | No covering | X | ○ |
| | Dispersing agent | — | | |
| | Solvent | — | | |

From the results shown in Table 1, the following is found. Comparative example 1 had excellent durability, but it had a poor polishing state. Comparative Example 2 had a good polishing state, but it had poor durability. Therefore, it was shown that both Comparative Examples 1 and 2 were not suitable for use. On the other hand, it was shown that Examples 1 to 14 had excellent durability and polishing properties. Particularly, it was shown that Examples 5 to 14 in which m was 7 or more had particularly excellent durability.

REFERENCE SIGNS LIST 1 core
2 cladding
3 covering layer
4 fluorinated alkylsilane layer
5 crack
11 jacket tube
12 ferrule
13 optical transmission element
15 endoscope
16 image guide
17 light guide
18 forceps port
19 nozzle
20 tip element

What is claimed is:

1. An optical transmission element comprising:
a fiber including a core made of glass and a cladding made of glass covering an outer periphery of the core; and
a covering layer covering an outer periphery of the cladding and including a plurality of alkyl groups which are not fluorine-substituted wherein each of the alkyl groups is bonded to the cladding via a siloxane bond,
wherein the alkyl groups are represented by $CH_3(CH_2)_m$— wherein m is an integer of 7 or more.

2. The optical transmission element according to claim 1, wherein the fiber and the covering layer are free of lead.

3. The optical transmission element according to claim 1, further comprising a solid lubricant applied to an outer periphery of the covering layer.

4. An image guide wherein a plurality of the optical transmission elements according to claim 1 are bundled.

5. A light guide wherein a plurality of the optical transmission elements according to claim 1 are bundled.

6. An endoscope comprising at least one of the image guide according to claim 4 and the light guide according to claim 5.

7. A method of producing an optical transmission element, comprising:
applying a treatment liquid including alkylsilane which is not fluorine-substituted, to an outer periphery of a cladding of a fiber to form a covering layer, wherein the fiber includes a core made of glass and the cladding made of glass covering an outer periphery of the core;
wherein the alkylsilane is represented by $CH_3(CH_2)_m Si(OR)_n(R')_{3-n}$ wherein m is an integer of 7 or more, n is an integer of 0 to 3, R each respectively represent —$CH_3$ or —$CH_2CH_3$, and R' each respectively represent —H, —$CH_3$ or —$CH_2CH_3$.

8. The method of producing an optical transmission element according to claim 7, wherein the treatment liquid includes the alkylsilane, a surfactant, and water.

* * * * *